(12) United States Patent (10) Patent No.: US 8,075,528 B2
Widenhouse et al. (45) Date of Patent: Dec. 13, 2011

(54) SURGICAL ACCESS PORT WITH FLEXIBLE SEALING CANNULA

(75) Inventors: Christopher W. Widenhouse, Clarksville, OH (US); Frederick E. Shelton, IV, Hillsboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 282 days.

(21) Appl. No.: 12/261,717

(22) Filed: Oct. 30, 2008

(65) Prior Publication Data

US 2010/0114032 A1 May 6, 2010

(51) Int. Cl.
*A61M 39/00* (2006.01)
(52) U.S. Cl. .............................. 604/164.03; 604/164.11
(58) Field of Classification Search .................. 604/103.03–103.05, 104–109, 604/164.11, 165.05, 167.03–167.06, 164.01–164.03; 606/191
See application file for complete search history.

(56) References Cited

U.S. PATENT DOCUMENTS

| 5,320,611 | A | 6/1994 | Bonutti et al. |
| 5,342,315 | A | 8/1994 | Rowe et al. |
| 5,628,732 | A | 5/1997 | Antoon, Jr. et al. |
| 6,808,508 | B1 * | 10/2004 | Zafirelis et al. ............... 604/131 |
| 7,163,525 | B2 | 1/2007 | Franer |
| 7,371,227 | B2 | 5/2008 | Zeiner |
| 2003/0216770 | A1 | 11/2003 | Persidsky et al. |
| 2004/0199121 | A1 * | 10/2004 | Wenchell et al. ........ 604/167.06 |
| 2005/0059865 | A1 * | 3/2005 | Kahle et al. ................... 600/206 |
| 2006/0247673 | A1 | 11/2006 | Voegele et al. |
| 2009/0082731 | A1 | 3/2009 | Moreno |

* cited by examiner

*Primary Examiner* — Nicholas D Lucchesi
*Assistant Examiner* — Melissa A Snyder

(57) ABSTRACT

A surgical access device for surgical instruments comprises a housing with an instrument port and zero closure valve. A cannula is disposed distally relative the housing. The cannula comprises a distal end, a proximal end, and a flexible tube having a longitudinal axis between the distal and proximal ends. An instrument seal is positioned adjacent the distal end of the cannula. The instrument seal is dimensioned to have an interference fit with a surgical instrument inserted into the cannula. Longitudinal movements of a surgical instrument are accommodated by buckling of the flexible tube while the relative longitudinal position of the instrument seal and instrument are substantially unchanged.

12 Claims, 5 Drawing Sheets

SURGICAL ACCESS PORT WITH FLEXIBLE SEALING CANNULA

BACKGROUND

The present invention relates in general to surgical devices and procedures, and more particularly to access devices.

Surgical procedures are often used to treat and cure a wide range of diseases, conditions, and injuries. Surgery often requires access to internal tissue through open surgical procedures or endoscopic surgical procedures. The term "endoscopic" refers to all types of minimally invasive surgical procedures including laparoscopic and arthroscopic procedures. Endoscopic surgery has numerous advantages compared to traditional open surgical procedures, including reduced trauma, faster recovery, reduced risk of infection, and reduced scarring. Endoscopic surgery is often performed with an insufflatory fluid present within the body cavity, such as carbon dioxide or saline, to provide adequate space to perform the intended surgical procedures. The insufflated cavity is generally under pressure and is sometimes referred to as being in a state of pneumoperitoneum. Surgical access devices are often used to facilitate surgical manipulation of internal tissue while maintaining pneumoperitoneum. For example, trocars are often used to provide a port through which endoscopic surgical instruments are passed. Trocars generally have an instrument seal, which prevents the insufflatory fluid from escaping while an instrument is positioned in the trocar, and a zero closure valve, which prevents the insufflatory fluid from escaping in the absence of an instrument.

While surgical access devices are known, no one has previously made or used a surgical access device in accordance with the present invention.

BRIEF DESCRIPTION OF DRAWINGS

While the specification concludes with claims which particularly point out and distinctly claim the invention, it is believed the invention will be better understood from the following description taken in conjunction with the accompanying drawings illustrating some non-limiting examples of the invention. Unless otherwise indicated, the figures are not necessarily drawn to scale, but rather to illustrate the principles of the invention.

DETAILED DESCRIPTION

Figure 1:
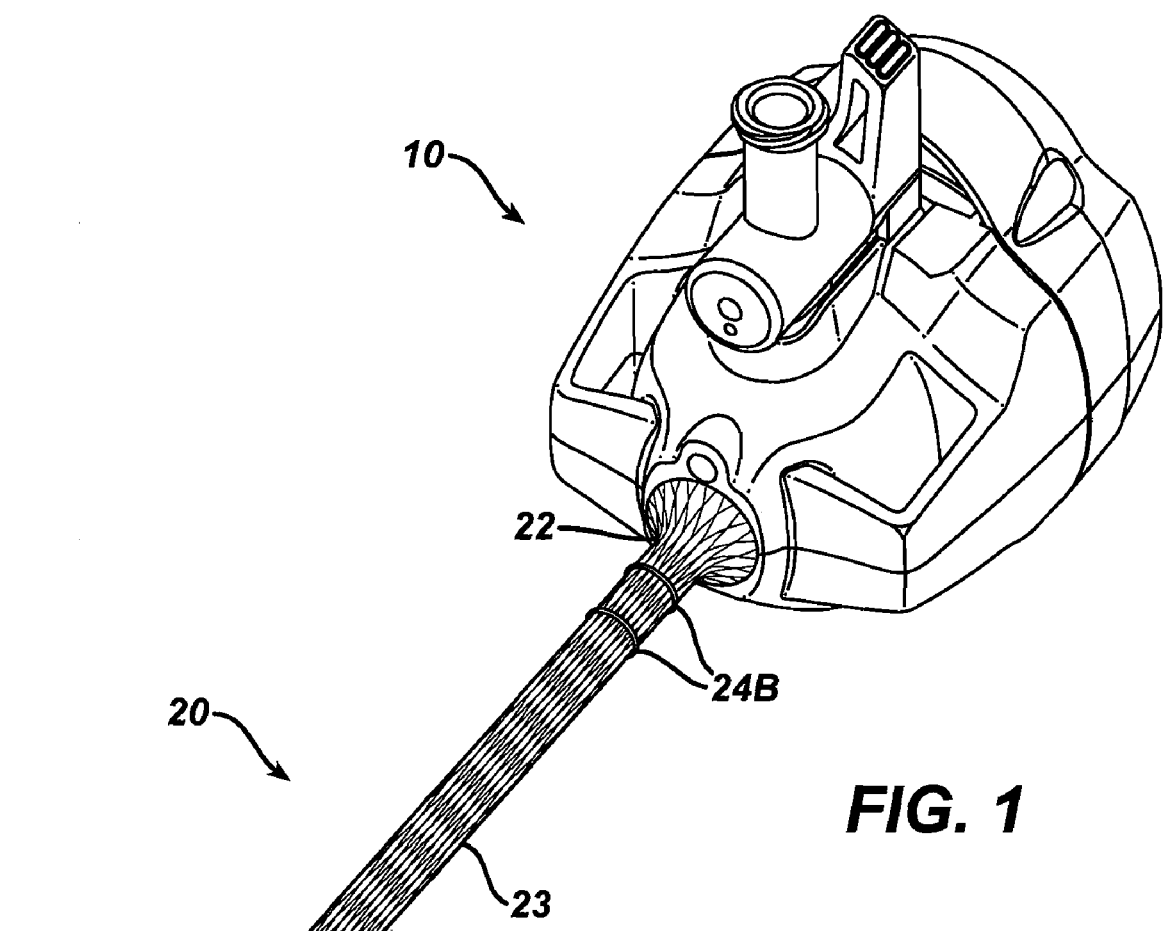
FIG. 1 depicts a perspective view of a surgical access device.

FIG. 1 illustrate an example of a surgical access device. The device includes a proximal housing (10) having an instrument port and a zero closure valve. The type of zero closure valve is not important, but one example of a suitable zero closure valve is a duckbill valve. A cannula (20) includes a distal end (21), a proximal end (22) attached to the housing (10), and tube (23) length extending between the proximal and distal ends (21, 22). The access device may include an obturator (not shown) that is slidably disposed through the cannula (20) and that has a distal end that extends beyond the distal end (21) for penetrating through tissue, such as the abdominal wall. Once inserted, the obturator can be removed from the cannula (20) so that the cannula (20) provides a working channel through the tissue for inserting various instruments.

The cannula (20) is a flexible tube (23) of material. Non-limiting examples include non-braided continuous sleeve of silicone, polyurethane, natural rubber, synthetic rubber such as polyisoprene, and the like. The embodiment illustrated in FIG. 1 has a cannula (20) which is a braided tube (23). The braided tube (23) can be formed in a variety of ways, but in one embodiment it can be formed by interweaving a plurality of filaments (18) around a central mandrel via a braiding machine. The interwoven braided filaments (18) can be spaced so as to allow the filaments (18) to move relative to each other. The term "filament (18)" as used herein is broadly defined to cover any element with an elongated configuration, including but not limited to a thread, fiber, cord, string, yarn, twine, rope, line, cable, wire, ribbon, tape, or the like. The filaments (18) in the braided tube (23) may all be the same type and material, or a composite of different of types or materials. By way of non-limiting example, a maypole type of braiding machine, as sold by Steeger USA, Inc. of Spartanburg, S.C., or by the New England Butt Division of Wardwell Braiding Machine Company, can be used in construction of the braided tube (23). A person of ordinary skill in the art will appreciate that braiding machines of this type use two groups of carriers, where each carrier carries a spool of the filament (18) to be presented by the respective carrier. Carriers are arranged in a circular array around a braiding axis of the central mandrel and are driven in one direction about that axis. Carriers of the first group are arrayed around the braiding axis and are driven in clockwise direction for example. Carriers of the second group are also arrayed, in a circular array around the braiding axis, in an alternating order with respect to carriers of the first group, and are driven in the opposite direction about the braiding axis. As the carriers move, the filaments (18) are pulled off their respective spools and laid out onto the central mandrel forming the braided tube (23). A person skilled in the art will also appreciate any type of machine capable of forming the braided tube (23) can be used in place of a maypole type braiding machine described above.

The filaments (18) used to make the braided tube (23) can also be formed from a variety of materials. By way of non-limiting example, the filaments (18) can be formed from polyester, cotton, polyamide, polyalkane, polyurethane, PET, PBT, nylon, PEEK, PE, glass fibre, metal wire, acrylic materials, and the like, or any composition of the mentioned materials. They may be in the form a monofilament or a multifilament and may have a cross section in the shape of any geometrical form, such as a cross section in the form of a rectangle, square or a circle. For instance, in case of a circle they may have a diameter range of about 0.005 to about 0.04 inches. A person skilled in the art will appreciate that the porosity of the braided tube (23) and the size of the windows (i.e., the spaces between the interlaced filaments (18)) formed by the intersecting filaments (18) are a function of the perpendicular distance (d) between the parallel filaments (18), the thickness of the filaments (18), and the intersection angle (A). The arrangement of the filament (18) braiding will change the characteristics of the braided flexible tube (23). For example, the porosity of the braided tube (23) influences its flexibility and its hoop strength. For instance, if all other variables are held constant, the lower the porosity of a braided tube (23) then the higher its hoop strength becomes. Decreasing the initial intersection angle (A), increasing the thickness of the filaments (18) or their numbers, and decreasing the perpendicular distance between the parallel filaments (18) are all ways to reduce the porosity of the braided flexible tube (23). In one embodiment, the intersection angle (A) has an angle range of more than 0 degrees and less than 0 degrees. In another embodiment, the intersection angle range between 10 and 170 degrees.

The particular shape and size of the braided tube (23) can also vary. In an exemplary embodiment, the braided tube (23) is cylindrical and has a diameter that is consistent along its length. However, in other embodiments, a portion of the braided tube (23) can be flared outward, such as a proximal end (22) of the braided tube (23), to facilitate attachment to the housing (10). The particular length and diameter will vary depending on the intended use. For instance, the size of the braided tube (23) can also vary depending on the tissue through which the braided tube (23) will be inserted. In an exemplary embodiment, the length is in the range of about 50 mm to 150 mm, and the diameter is in the range of about 5 mm to 25 mm.

Figure 1A:
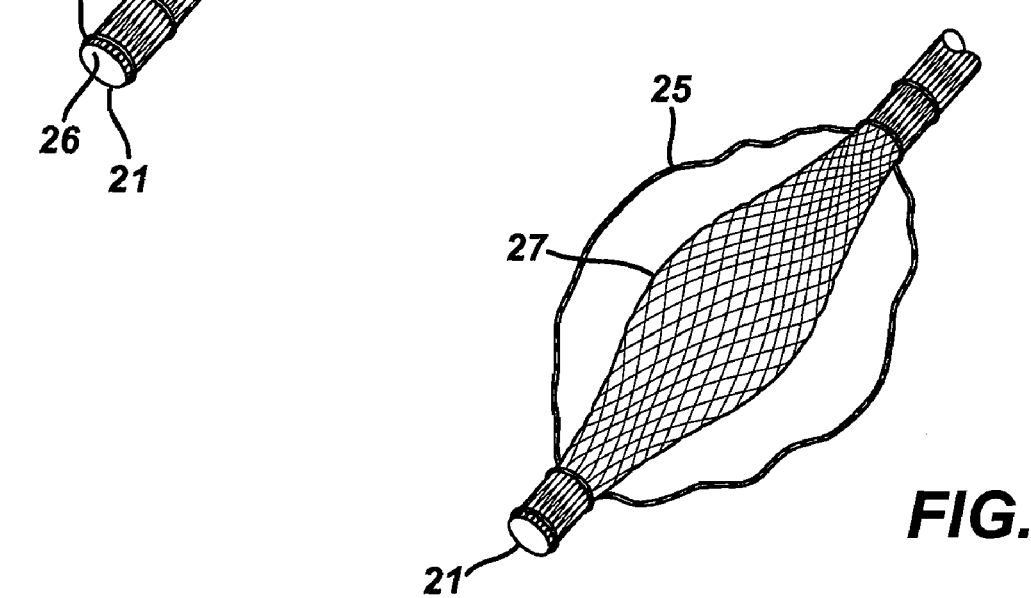
FIG. 1A depicts a variation of the surgical access device of FIG. 1.
Figure 2:
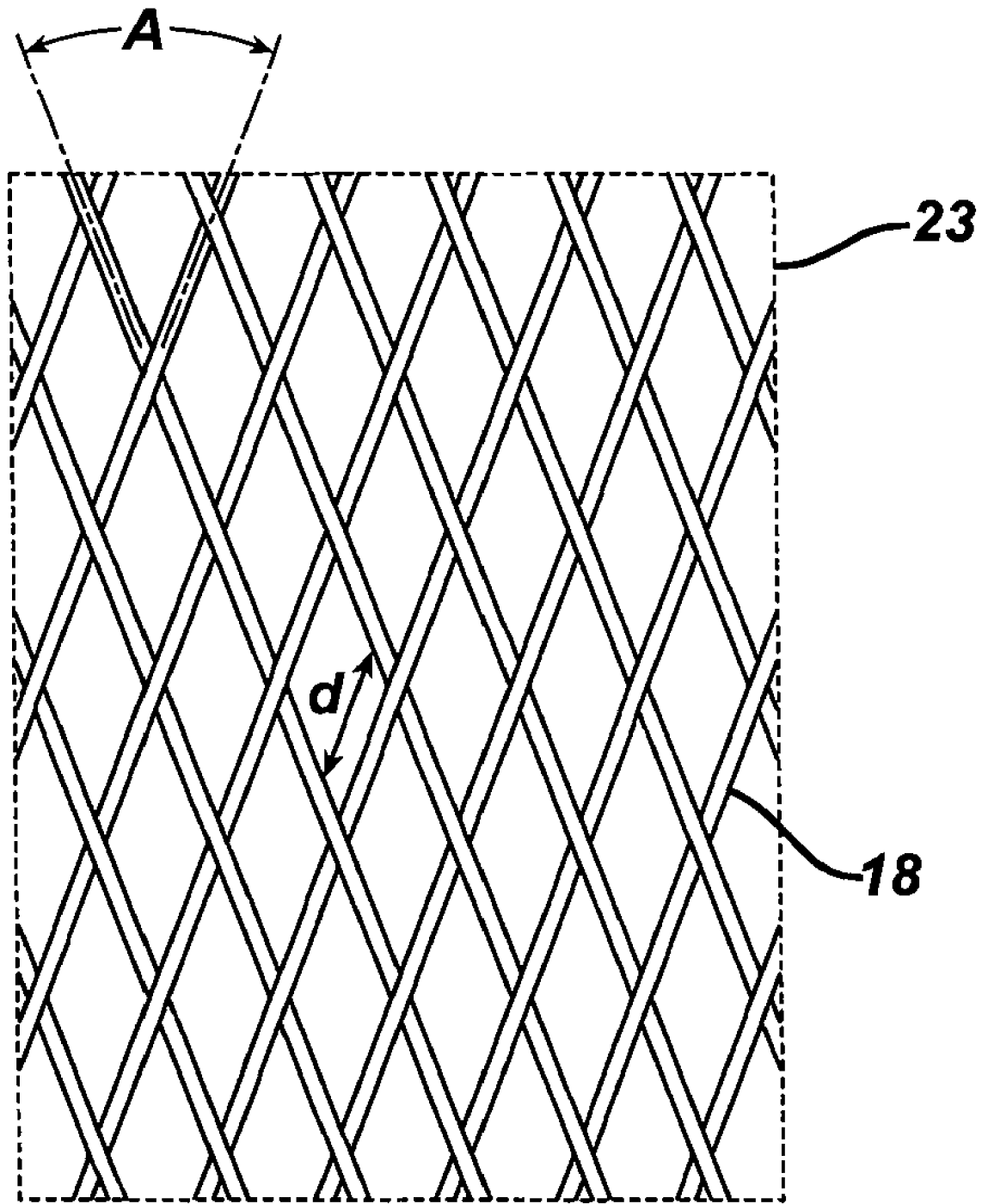
FIG. 2 depicts a portion of a braided tube.

The braided tube (23) can also include features to provided a barrier between the tissue and the braided tube (23) such that the sidewall of the braided tube (23) is substantially fluid impermeable. In one embodiment, the braided tube (23) can include a flexible sheath disposed around an inner or outer sidewall of the braided tube (23) that provides a substantially fluid impermeable barrier to prevent fluid from flowing through the sidewall of the braided tube (23). The flexible sheath can be made from a variety of materials, such as, for example, an elastomeric sheath. In another embodiment, the braided tube (23) can include a coating formed thereon to provide a substantially fluid impermeable barrier. The coating can be formed from a variety of materials, such as a polymer coating that provides a smooth outer and/or inner surface to the braided tube (23). For instance, the braided tube (23) may be dipped into a polymer solution. Polymers that may be used include, by way of non-limiting example, biocompatible polymers such as polyvinyl chloride, polyolefin (e.g., polyethylene, polypropylene, ethylene-vinylacetate copolymer), polyamide, polyester (e.g., polyethylene terephthalate (PET), polybutylene terephthalate), polyurethane, polystyrene resin, fluoro-based resin (e.g., polytetrafluoroethylene, ethylene-tetrafluoroethylene copolymer), polyimide, and the like; and various elastomers such as polyurethane-based elastomer, polyester based elastomer, polyolefin-based elastomer, polyamide-based elastomer, silicone rubber, latex rubber, and the like. FIG. 1A shows a variation in which a flexible sheath (25) is loosely disposed laterally about the braided tube (23).

Adjacent the distal end (21) is an instrument seal (26). In this embodiment the instrument seal (26) is provided by a coating of a flexible and resilient polymer on the inner surface of the tube (23). The inside diameter of the distal end (21) is preferably dimensioned to be slightly smaller than the smallest diameter instrument intended to be sealed in cannula (20). Accordingly, an interference fit is provided between the seal (26) and the instrument thus providing a seal preventing the escape of insufflatory fluids. Optionally, resilient bands (24A) may be added to increase hoop stresses thus biasing the seal (26) against the instrument to facilitate a better seal. Preferably, the distal end (21) and the seal (26) are sufficiently flexible and resilient to accommodate a numerous sizes of instruments ranging from about 5 mm and about 12 mm, and more preferably from about 3 mm to about 15 mm.

An interference fit between the instrument seal an the instrument necessarily induces a frictional resistance to relative motion. As an instrument is inserted into the housing (10), through the cannula (20), and out the distal end (21), the tube (23) will remain taut between the seal and the housing (10), as shown in FIG. 1, thus counteracting the frictional resistance. The instrument may be continued to be advance distally to the full insertion length contemplated for the surgical procedure. When the instrument is then moved proximally the seal will frictionally engage the instrument and maintain its relative longitudinal position. The proximal motion is accommodated by the tube (23) buckling resulting in one or more lateral bulges (27). Thereafter, as the instrument is longitudinally moved back and forth during a surgical procedure, the motion is accommodated by the increasing and decreasing the size of the bulge (27). Likewise, rotational motion of the instrument can be accommodated by twisting of the tube (23). Preferably, the force required buckle the tube (23) will be less than the frictional resistance induced by the inference between the seal (26) and an instrument. Accordingly, the surgeon will be required to exert less force in using and instrument compared to sliding the instrument over the seal (26), thus facilitating improved tactile feedback and fine instrument control. To remove the instrument, the instrument is retracted proximally until the bulge (27) forms a flange against the peritoneal surface of the abdominal wall thus fixing the distal end (21) sufficient to overcome the frictional resistance as the instrument is proximally retracted from the cannula (20).

Figure 3:
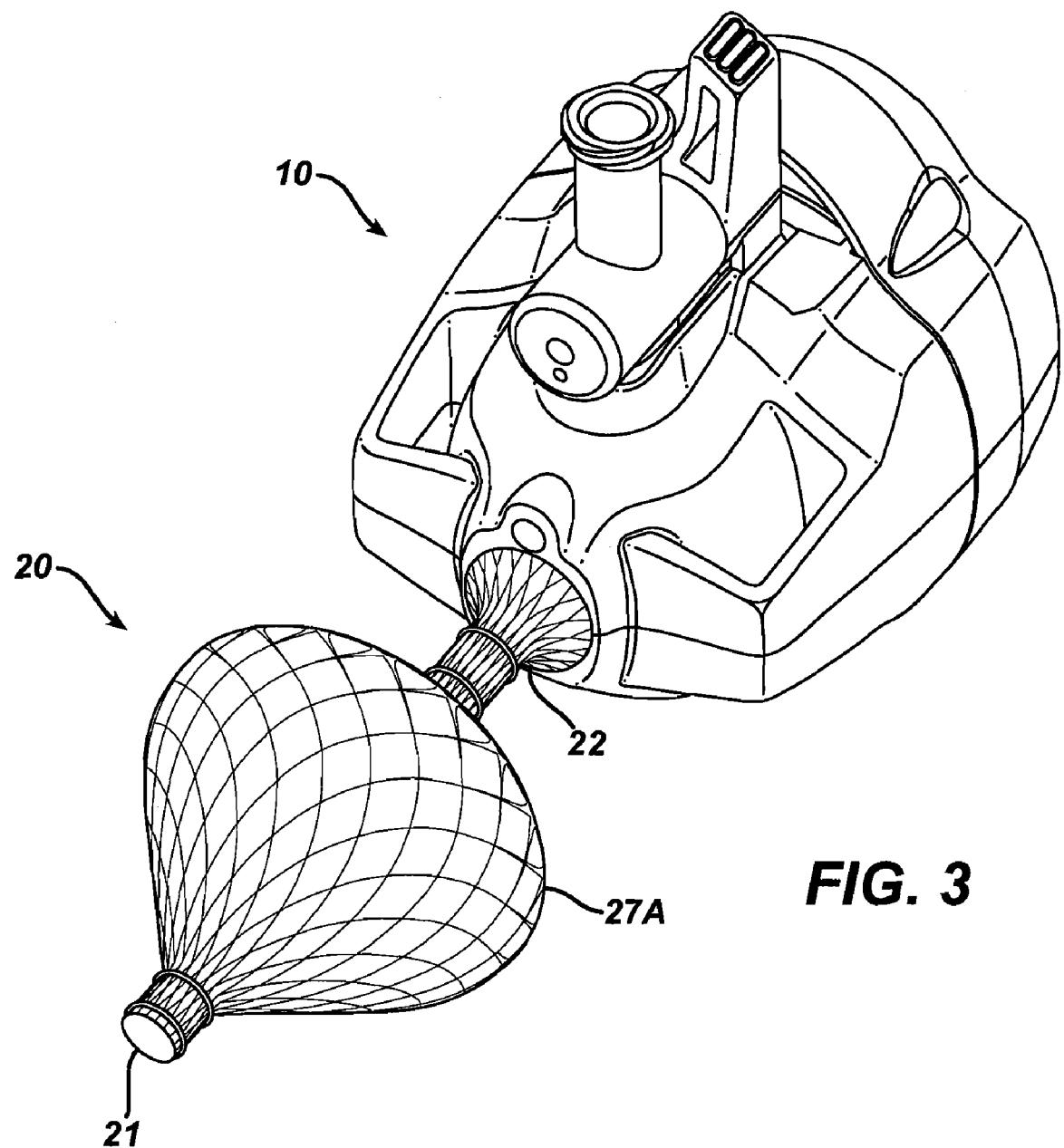
FIG. 3 depicts a perspective view of a surgical access device with a buckled cannula.
Figure 4:
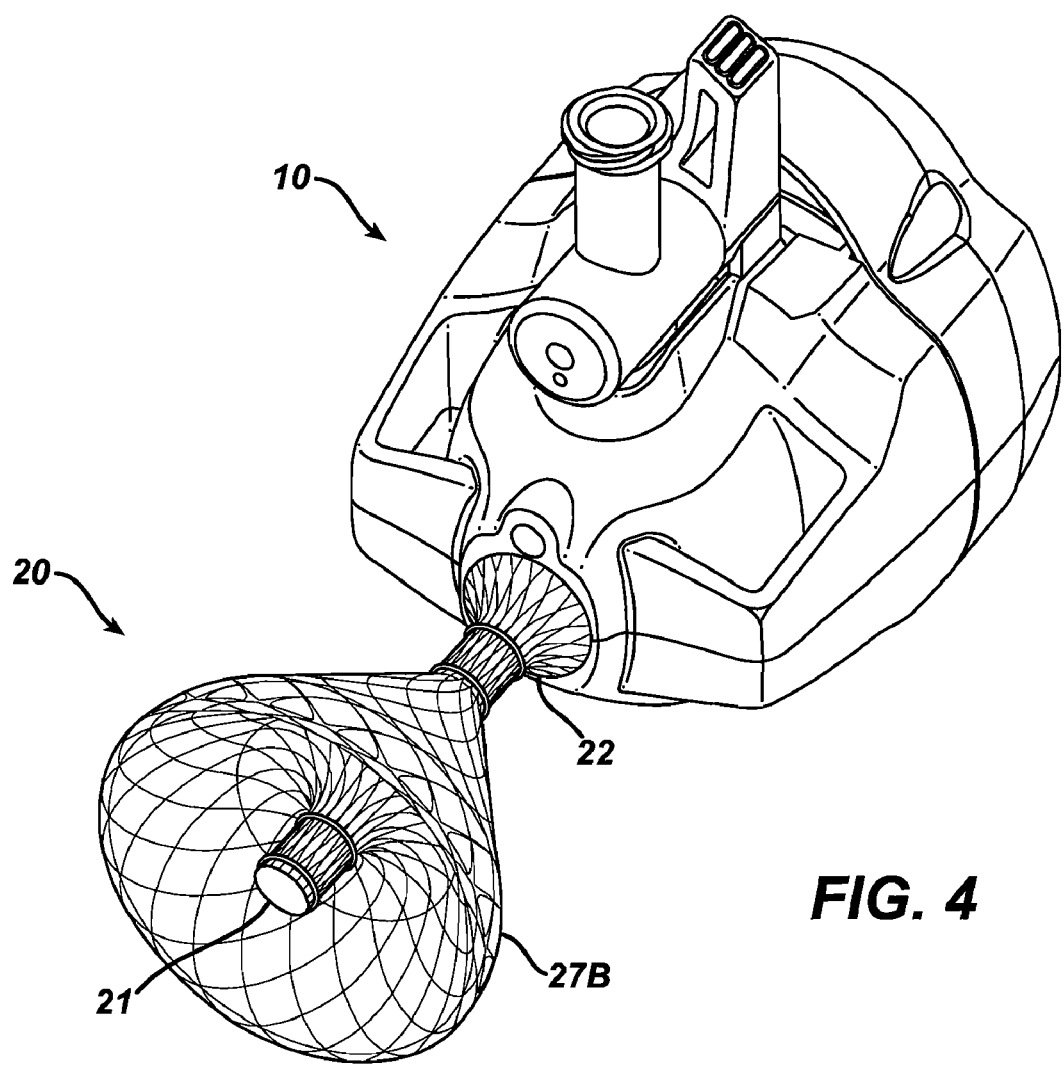
FIG. 4 depicts a perspective view of a surgical access device with a buckled cannula.

The shape and location of the bulges (27) can be controlled by optional bands (24B). The shape and location of bulges (27) may be further configured by a longitudinally asymmetrical tube (23), including without limitation varying filament materials or dimensions, varying braid patterns, adding, removing or changing coatings, and the like. For instance, FIG. 1A illustrates a substantially symmetrical bulge (27), but FIGS. 3-4 illustrate asymmetrical bulges (27A, 27B). The bulge (27A) includes a proximally oriented concave face, while the bulge (27B) includes a distally oriented concave face. Such features may facilitate fixation for instrument removal and improved visualization of the distal end (21).

Figure 5:
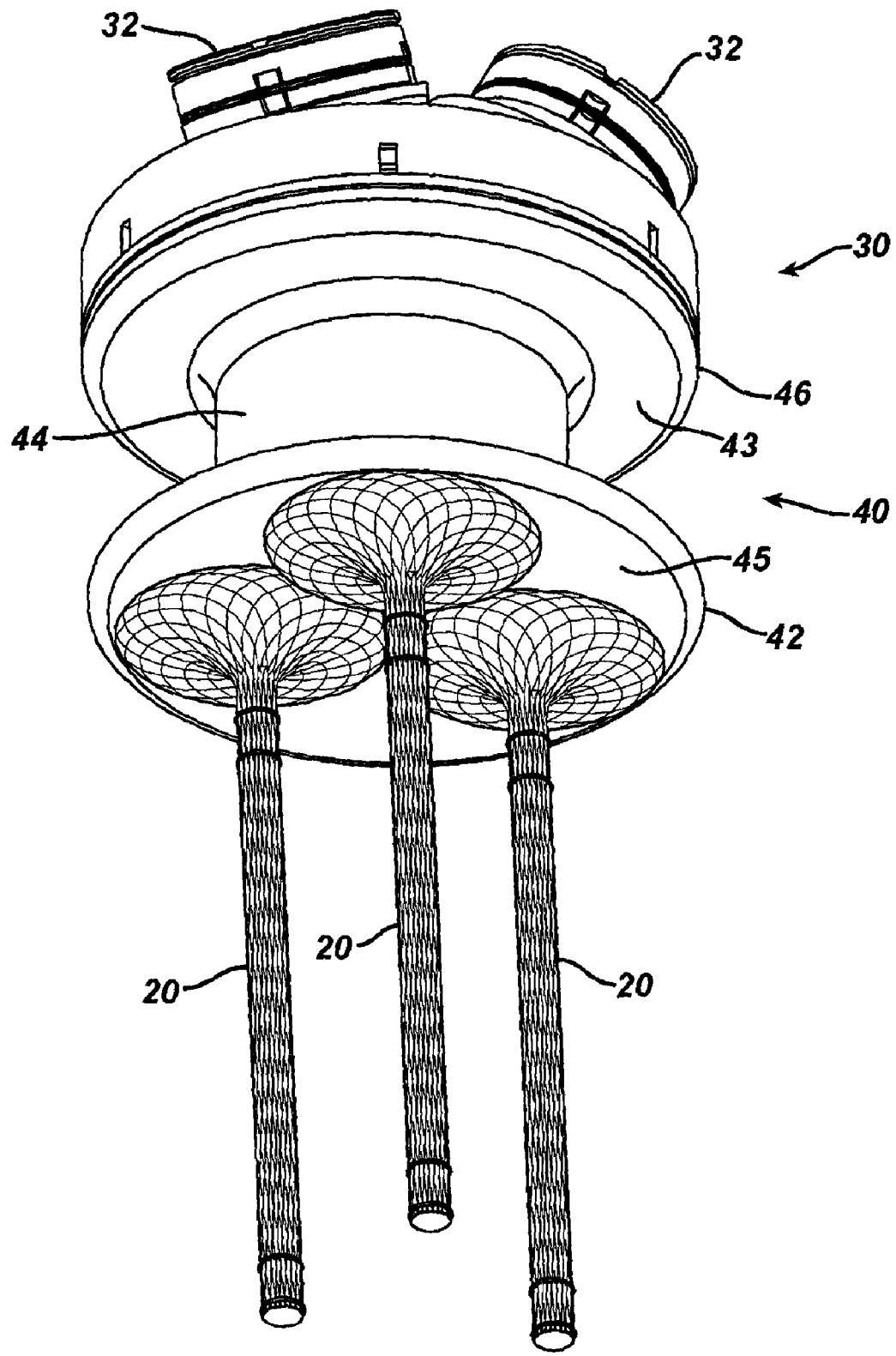
FIG. 5 depicts a perspective view of a multi-port surgical access device.

FIG. 5 illustrates a surgical access device comprising a housing (30), a wound protector (40), and multiple cannulas (20) similar to the prior embodiments. The access device is capable of accommodating multiple instruments through a single incision. The housing (30) includes multiple instrument ports (32) each having a zero closure valve. In this embodiment the number of instrument ports (32) is equal to the number of cannulas (20), shown here as three. The wound protector (40) is separate from the cannulas (20), and in this example is a flexible fixed length type of wound protector having a distal ring (42), a proximal ring (46), and a flexible sleeve (44) extending between the distal and proximal rings (42, 46). Naturally, other types of known wound protectors may also be used, including without limitation flexible roll-up wound protectors, flexible variable length pull-up types of wound protectors, rigid cannulas, and the like. As an example of use in abdominal surgery, the wound protector (40) could be placed in an incision in the abdominal wall such that the distal ring (42) is adjacent the peritoneal surface and the proximal ring (46) is adjacent the cutaneous surface. The proximal and distal rings (42, 46) are laterally disposed relative the incision to define a flanges (43) that facilitate holding the wound protector (40) in the incision. In this embodiment the proximal ring (46) and distal ring (42) are circular; however, non-circular rings are also possible. The distal face (45) is closed except for the cannulas (20). In use an instrument is passed through a port (32) and into the one of the cannulas (20). Accordingly, three instruments may be simultaneously used through a single incision.

Having shown and described various embodiments and examples of the present invention, further adaptations of the methods and devices described herein can be accomplished by appropriate modifications by one of ordinary skill in the art without departing from the scope of the present invention. Several of such potential modifications have been mentioned, and others will be apparent to those skilled in the art. For instance, the specific materials, dimensions, and the scale of drawings will be understood to be non-limiting examples. Accordingly, the scope of the present invention should be considered in terms of the following claims and is understood not to be limited to the details of structure, materials, or acts shown and described in the specification and drawings.

The invention claimed is:

1. A surgical access device for surgical instruments, comprising:
   a) a housing with an instrument port and zero closure valve;
   b) a cannula disposed distally relative the housing, the cannula comprising a distal end, a proximal end, and a flexible tube having a longitudinal axis between the distal and proximal ends;
   c) an instrument seal positioned adjacent the distal end of the cannula, the instrument seal being dimensioned to have an interference fit with a surgical instrument inserted into the cannula;
   wherein the longitudinal movements of a surgical instrument are accommodated by buckling of the flexible tube resulting in one or more lateral bulges spaced from the instrument while the longitudinal position of the instrument seal relative to the instrument is substantially unchanged.

2. A surgical access device of claim 1, wherein the flexible tube is braided.

3. A surgical access device of claim 2, further comprising a flexible sheath disposed relative the braided tube providing a substantially fluid impermeable barrier.

4. A surgical access device of claim 3, wherein the flexible sheath is loosely disposed laterally about the braided tube.

5. A surgical access device of claim 1, wherein the flexible tube buckles with a symmetrical lateral bulge.

6. A surgical access device of claim 1, wherein the flexible tube buckles with an asymmetrical lateral bulge.

7. A surgical access device of claim 6, wherein the bulge comprises a proximally oriented concave face.

8. A surgical access device of claim 1, wherein the instrument seal can accommodate a numerous sizes of surgical instruments ranging from about 5 mm to about 12 mm.

9. A surgical access device of claim 1, wherein the housing comprises a plurality of instrument ports a corresponding number of zero closure valves and cannulas.

10. A surgical access device of claim 1, further comprising a wound protector separate from the cannula.

11. A surgical access device, comprising:
   a) an housing with an instrument port;
   b) a cannula disposed distally relative the housing, the cannula comprising a distal end, a proximal end, and a flexible braided tube extending between the distal and proximal ends;
   c) an instrument seal positioned adjacent the distal end of the cannula;
   wherein longitudinal movements of a surgical instrument are accommodated by buckling of the flexible braided tube resulting in one or more lateral bulges spaced from the instrument while the longitudinal position of the instrument seal relative to the instrument is substantially unchanged.

12. A surgical access device of claim 11, further comprising a flexible sheath disposed relative the braided tube providing a substantially fluid impermeable barrier.

* * * * *